United States Patent [19]

Mixich et al.

[11] Patent Number: 5,550,227
[45] Date of Patent: Aug. 27, 1996

[54] METHOD FOR THE PREPARATION OF RHAMNOSE MONOHYDRATE FROM RHAMNOLIPIDS

[75] Inventors: Johann Mixich, Kelkheim; Knut M. Rapp, Offstein; Manfred Vogel, Neuleiningen, all of Germany

[73] Assignee: Südzucker AG Mannheim/Ochsenfurt, Mannheim, Germany

[21] Appl. No.: 250,104

[22] Filed: May 26, 1994

Related U.S. Application Data

[63] Continuation of Ser. No. 977,401, filed as PCT/EP91/01426, Jul. 30, 1991 published as WO92/05182, Apr. 2, 1992, abandoned.

[30] Foreign Application Priority Data

Sep. 25, 1990 [DE] Germany .................. 40 30 262.8

[51] Int. Cl.$^6$ .................. C07H 1/00; C07H 1/06; C07H 1/08; C13K 13/00
[52] U.S. Cl. .................. 536/124; 536/1.11; 536/128; 127/34; 127/36
[58] Field of Search .................. 536/124, 128, 536/4.1, 8, 1.11; 435/99, 74, 75, 105, 267, 274; 127/34, 36

[56] References Cited

U.S. PATENT DOCUMENTS

| | | | |
|---|---|---|---|
| 4,758,283 | 7/1988 | Takemura et al. | 536/128 |
| 4,772,334 | 9/1988 | Hatanaka et al. | 536/124 |
| 4,814,272 | 3/1989 | Wagner et al. | 435/74 |
| 4,933,281 | 6/1990 | Daniels et al. | 536/123 |
| 5,077,206 | 12/1991 | Cheetham et al. | 536/128 |

*Primary Examiner*—John Kight
*Assistant Examiner*—Everett White
*Attorney, Agent, or Firm*—Finnegan, Henderson, Farabow, Garrett & Dunner, L.L.P.

[57] ABSTRACT

The invention relates to a method for the preparation of rhamnose from rhamnolipids, for which an acidic emulsion of the rhamnolipid is hydrolyzed at 100° to 200° and subsequently cooled, the aqueous phase of the resulting hydrolysate is separated from the lipid phase, its pH is raised by the addition of a basic compound, any precipitate formed is removed, the remaining solution is concentrated and either processed further directly or chromatographed on ion exchange resin, rhamnose-containing fractions being obtained as eluate, which are processed further as such or worked up into crystalline rhamnose monohydrate.

26 Claims, 1 Drawing Sheet

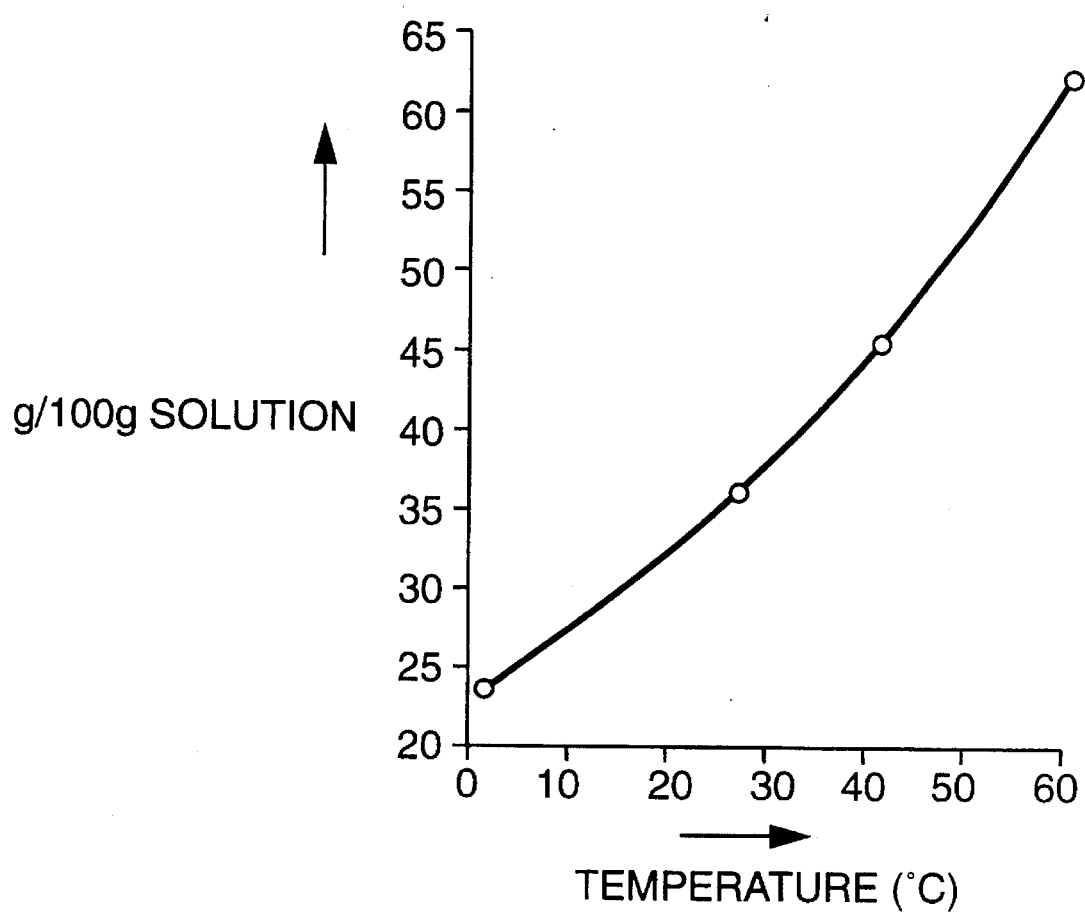

METHOD FOR THE PREPARATION OF RHAMNOSE MONOHYDRATE FROM RHAMNOLIPIDS

This application is a continuation of application Ser. No. 07/977,401, filed as PCT/EP91/01426, Jul. 30, 1991, published as WO92/05182, Apr. 2, 1992, now abandoned.

Rhamnose is a 6-desoxy sugar (monosaccharide), which occurs in nature in the D as well as in the L form.

The preparation of L-rhamnose, which is the most readily accessible 6-desoxymonosaccharide at the present time, is the object of various patent applications. One of the materials, which can be prepared from such desoxy sugars, is 2,5-dimethyl-4-hydroxy-2,3-dihydrofuran-3-one (furaneol), which finds use as an aroma or flagrance material.

As starting material for a recovery of rhamnose, various natural materials come into consideration, for example, glycosides such as rutin, quercitrin, naringin, hesperidin and polysaccharides such as gum arabic, the fermentatively obtained polysaccharide S-60 (U.S. Pat. No. 4,326,053) or rhamnolipids, which are produced fermentatively or microbially, for example, from bacteria of the Pseudomonas type, for example, from natural oils or crude oil fractions.

Independently of the type of the aforementioned starting materials, a hydrolysis, which can be catalyzed enzymatically or acidically, is required for obtaining the rhamnose, a mixture being obtained, which, aside from rhamnose, contains also other substances.

If one starts out from glycosides containing rhamnose, one is dependent on vegetable starting materials, such as the waste products of citrus manufacture, which are obtainable only in the seasonal rhythm and the composition of which varies within wide limits. In order to be independent of such fluctuations, it is more advantageous to use fermentatively obtained polysaccharides or rhamnolipids, which can be produced reproducibly, as starting materials.

Compared to the use of rhamnose-containing heteropolysaccharides, the use of rhamnolipids has the advantage that the desired sugar-rhamnose—does not have to be separated after a hydrolysis from other sugars, such as glucose and mannose, which otherwise are present in many cases in substantial amounts in the hydrolysis solution. The separation of a complex sugar mixture is technically more complicated than the isolation of rhamnose from the hydrolysate of a rhamnolipid.

A rhamnolipid, particularly a fermentatively obtained rhamnolipid, thus is a very suitable starting material for the production of rhamnose.

Aside from a suitable starting material, the possibility of isolating the rhamnose easily from a hydrolysate of complex composition is of quite decisive importance for the production of rhamnose on an industrial scale.

The following methods have been described for the recovery of rhamnose from hydrolysate.

According to the German Offenlegungsschrift 35 45 107, a large amount, particularly a 5- to 20-fold amount, based on the aqueous phase, of a polar organic solvent is added to the neutralized aqueous hydrolysate. After that, the solvent is removed, the sugar is separated on a strongly acidic cationic exchanger, preferably using acetone or acetonitrile as "extraction agent", and the rhamnose is purified by adsorption on activated charcoal. This working up method is cumbersome and not suitable for an economic recovery of rhamnose.

According to the EP-A 317 033, the glycosides contained in citrus waste are hydrolyzed enzymatically for the recovery of rhamnose. The glucose contained in the hydrolysate is removed by fermentation with yeast or by selective oxidation of the glucose to 5-ketogluconic acid. This method is expensive and cumbersome, particularly as a chromatographic purification using activated charcoal is required.

According to the EP-A 282 942, which corresponds to U.S. Pat. No. 4,933,281 an isolated rhamnolipid is used as starting material, which is hydrolyzed with $H_2SO_4$ at 30° to 100° C. The thereby resulting hydroxydecanoic acid is either extracted with ethyl acetate or adsorbed on anionic exchangers. The hydrolysis of the rhamnolipid precipitate (Example III) takes place in very dilute solution. Rhamnose-containing precipitate (1.9 g) is suspended in 300 mL of molar $H_2SO_4$, heated and subsequently treated with the four-fold volume of 1,200 mL of ethyl acetate. In the aqueous phase, 1.2 g of rhamnose are found, while 0.5 g of rhamnose remain in the organic (ethyl acetate) phase.

The amounts of acid and solvent required for the preparation of only 1.2 g of rhamnose make it impossible to produce rhamnose economically in this way.

Up to now, therefore, no method is known, which permits rhamnose to be produced in large amounts with economic means and without expensive and dangerous auxiliaries (enzymes, flammable and poisonous solvents).

The object of the invention now is a method for the preparation of rhamnose from rhamnolipids, which is characterized in that an acidic emulsion of the rhamnolipid is hydrolyzed at 100° to 200° C. and subsequently cooled, the aqueous phase of the resulting hydrolysate is separated from the lipid phase, its pH is raised by the addition of a basic compound, any precipitate formed is removed, the remaining solution is concentrated and either processed further directly or chromatographed over an ion exchange resin, rhamnose-containing fractions being obtained as eluate, which are processed further as such or worked up into crystalline rhamnose monohydrate.

It is an advantage of the inventive method that it is possible to do completely without the use or organic solvents and that water can be used exclusively as solvent.

BRIEF DESCRIPTION OF THE DRAWINGS

FIG. 1 shows the solubility of L-rhamnose in water as a function of the temperature.

The rhamnolipids, used for the inventive method, can be prepared in various ways, for example, by the fermentative methods of EP-A 282 942, which corresponds to Daniels et al. U.S. Pat. No. 4,933,281, and of DE-A 34 05 664, which corresponds to Wagner et al. U.S. Pat. No. 4,814,272. Advisably, the emulsions obtained are largely freed from extraneous salts, advantageously to such an extent, that they have a conductivity of less than 12 mS/cm and preferably of less than 5 mS/cm. Such desalinated emulsions can also be prepared by the method of the Hoechst Aktiengesellschaft U.S. Pat. No. 5,440,028, which was filed on the same day under the title of "Method for the preparation of suitable glycolipids by membrane separation methods by ultrafiltration". For the inventive method, those emulsions are advisably used, the aqueous phase of which has a pH of 0 to 3 and preferably of 0.5 to 1.5, and a solids content, that is, an evaporation residue that is determined by heating for 30 minutes at 85° C. and 6 kPa, of 5 to 50 and preferably of 10 to 60% by weight. The total solids concentration can be adjusted to this value by evaporation or by dilution with water.

The inventive method can be carried out discontinuously or continuously, the continuous method being preferred.

Hydrochloric acid, for example, can be used to adjust the pH of the emulsion to a value of 0 to 3; however, if it is intended to work continuously, it is advisable to use as acids those which form a salt of low solubility with the basic compound used in the later stage of the method, preferably $H_2SO_4$, $H_3PO_4$ and HF.

The acidic emulsion is heated, for example, discontinuously or continuously with good stirring for 5 to 300 minutes, preferably for 20 to 150 minutes and particularly for 30 to 120 minutes at a temperature of 100° to 200° C., preferably of 110° to 160° C. and particularly of 120° to 150° C. and subsequently cooled. Up to the separation of the aqueous phase from the oily phase, good mixing of the hydrolyzing mixture is very important, since this is a heterogeneous hydrolysis, in which the acid, which acts as catalyst, as well as the rhamnose, which is set free, are in the aqueous phase and the rhamnolipid, which is to be hydrolyzed, together with the unreacted substrate, such as soybean oil, is in the lipid phase. The mixing can be supported by physical means, such as by stirring, shaking or using ultrasound.

As in the case of the discontinuous method, the duration of the hydrolysis depends, of course on the temperature employed. For the continuous method, the residence time can be varied by changing the different factors, such as the output of the feed pump, the number of the reactors or the capacity up to the pressure-retaining valve.

After the hydrolysis a product is obtained, which consists essentially of an aqueous phase, which contains the rhamnose set free and, aside from which, an oil phase is still present, which contains, for example, unreacted rhamnolipid. This product is separated, for example in a separator, into the two phases. In order to make the separation process an easy one, the two phases are separated at a temperature less than 100° C. and preferably of about 50° to 90° C.

As basic compounds, particularly those are suitable, which form salts of low solubility with the acid used, preferably $Ca(OH)_2$ and/or $CaCO_3$. Such salts are preferred particularly for the continuous method. The pH is raised advisably up to a value of 2 to 8 and preferably up to a value of 3 to 7. The solids formed are separated, optionally with the addition of a filter aid, and the flitrate is concentrated under reduced pressure, preferably at a pressure of less than 20 kPa and a temperature of, for example, 60° C., to a solids content of 20 to 60% by weight and preferably of 25 to 50% by weight. As filter aids, those based on cellulose or diatomaceous earth, such as Arbocell® and Celit® come into consideration.

Suitable ion exchange resins are sulfonated polystyrene resins, cross linked with divinylbenzene, in the salt form, which preferably contain the same type of cations as the basic compound used for the neutralization. The rhamnose-containing fractions, obtained by chromatography, are concentrated under reduced pressure, preferably at a pressure less than 20 kPa, depending on the temperature, to a solids content of, for example, about 65% by weight, filtered if necessary and allowed to crystallize.

Before or after a chromatographic separation, the rhamnose can be processed further in this form, for example, to furaneol, if the purity of the solution is adequate.

As a preliminary purification of the aqueous phase before the chromatography and the crystallization, this phase can be treated with decolorizing agents, such as activated charcoal or bentonite.

The crystallization can be carried out as an evaporation crystallization and/or a cooling crystallization. The cooling crystallization is carried out preferably between 65° and 15° C. at a cooling rage of 1° to 10° C./hour and preferably of 3° to 6° C./hour. The evaporation crystallization can, for example, be carried out by evaporating water at a temperature of 65° C. and a pressure of 20 kPa at such a rate, that a supersaturation in the mother liquor of 1.05 to 1.3 and preferably of 1.1 to 1.15 is maintained and the crystals of rhamnose monohydrate can grow to an edge length of 0.3 to 0.5 mm. The crystallisate can be separated from the mother liquor in a perforated basket centrifuge. The mother liquor can be subjected to a second crystallization step. As is well known, such a multistep evaporation crystallization leads to a higher yield of crystalline product.

The residual mother liquor, thereafter obtained, can be freed from interfering extraneous substances by a chromatographic treatment and worked up further, as described above, to crystalline rhamnose monohydrate.

As crude product, rhamnose is obtained in the form of crystals of rhamnose monohydrate with a purity of about 95%. This crude crystallisate is recrystallized from water and dried in the usual manner, for example, by moving 70° C. air over it or under reduced pressure, for example, of less than 20 kPa, at a temperature of 20° to 70° C.

The method of continuous, acidic hydrolysis of a rhamnolipid is described more precisely in the following by way of example.

EXAMPLE 1

From a desalinated concentrate, obtained by fermentation and having a solids content of 40% by weight (determined gravimetrically), a rhamnolipid emulsion with a solids content of 15% by weight and a pH of 0.9 was prepared by stirring with sulfuric acid and water.

This emulsion was introduced at the rate of 380 L/hour by a Mohno pump into hydrolysis equipment, which consisted essentially of:
a) homogenizing equipment (for example a SUPRATON® machine) with a controlled steam injection in the suction side,
b) a hot-holding segment, consisting of several reactors, through which the emulsion passes consecutively and the last one of which has a pressure-retaining device (pressure-retaining valve), with which a particular pressure can be set between the Mohno pump and the pressure-retaining valve, in which the aqueous emulsion can be heated to 150° to 160° C., the residence time in the hot-holding segment being about 120 minutes, and
c) cooling equipment, such as a tubular cooler, with which the hydrolysate is cooled to a temperature below 100° C.

Tools, which bring about good homogenization and comminution, are built into the SUPRATON machine. This machine has the task of subjecting the product stream to high shear forces and thus mixing acid, water and rhamnolipid intimately. In this way, conditions are satisfied, which are of great importance for a heterogeneous reaction mixture.

The cooled hydrolysate was collected in a vessel equipped with a stirrer. The phases were then separated mechanically, for example, in a separator (such as a Westfalia separator) and the aqueous phase was drawn off continuously. This was collected in a vessel equipped with a stirrer and brought to a pH of 4.5 with calcium carbonate. The resulting precipitate (gypsum) was removed, for example, in a chamber filter press and washed and the flitrate was concentrated under reduced pressure (less than 20 kPa). Out of a total of 380 L/hour of the emulsion supplied to the hydrolysis plant, about 440 L/hour of hydrolysate and about 320 L/hour of flitrate are obtained. This was concentrated to a solids content of about 50% by weight, filtered and chromatographed on a Lewatit TSW 40 ion exchanger in the calcium form.

The equipment used for the chromatographic separation consists of 3 columns (1 m in diameter) with a total resin content of 14 m³.

A crude product with a solids content of 47.6% by weight is obtained in an amount of 700 kg (333 kg of total solids). The 244 kg of rhamnose contained are eluted with desalinated water at 65° C. at a flow rate of 1.6 ms/hour. The product fraction, which is obtained after a 0.5 L bed volume at the end of the 3rd column and amounts to 0.275 L of bed volume (3.85 m³, containing 210 kg of rhamnose) is concentrated gently and is caused to crystallize together with a further product fraction.

The concentrated product fraction (600 kg with a total solids content of 69.2% by weight and 457 kg of total solids) is cooled in a 600 L cooling crystallizer with stirring from 65° C. to 20° C. at a cooling rate of 3°/hour and subsequently separated in a particle size centrifuge into 354 kg of rhamnose monohydrate crystals and 365 kg of mother liquor (including washing water).

The crystals have a purity of 98% and are colored slightly yellow. They can be recrystallized from water. The mother liquor is subjected to a further crystallization and the final mother liquor resulting therefrom is chromatographed once again.

EXAMPLE 2

(Discontinuous Hydrolysis)

To a concentrate (40% total solids) desalinated by ultrafiltration, concentrated hydrochloric acid was added in such an amount, that the concentration of hydrochloric acid in the mixture as a whole was about ⅛ normal (0.46% by weight).

The emulsion was heated for 2 hours at 140° C. in an autoclave with stirrer. After cooling, the phases were separated. The pH of the aqueous phase was adjusted to a value of about 6 to 8 with calcium hydroxide. Bentonite was added to this phase, stirred for one hour and filtered off.

The flitrate has a pH of 6 to 8 and a total solids content of approximately 11% by weight and contains about 75 g of rhamnose/L. This solution was caused to crystallize directly. The mother liquor was chromatographed as in Example 1 and caused to crystallize as in Examples 1 or 3.

EXAMPLE 3

(Evaporization Crystallization)

In an evaporization crystallizer (100 L capacity), the concentrated product fraction with a total solids content of approximately 65% by weight was concentrated isobarically at 20 kPa, the level being maintained above the heating chamber. At a supersaturation of 1.1 (see solubility curve Figure), the product fraction was seeded with finely ground rhamnose monohydrate crystals. Subsequently, the concentrated product solution was added slowly in accordance with the rate of crystallization, until the boiler was filled. The total solids content of the magma then was about 80% by weight. The contents (magma) were subsequently separated in a particle size centrifuge into 27.8 kg of rhamnose monohydrate and 46.5 kg of mother liquor.

The mother liquor was crystallized a second time; the final mother liquor was freed from by-products by chromatography and the rhamnose was crystallized as described above.

We claim:

1. A method for preparing rhamnose from rhamnolipids comprising the steps of:

a) hydrolyzing an aqueous acidic rhamnolipid emulsion having a pH value of 0 to 3.0 at a temperature of 110° to 200° C. for a period of 5 to 300 minutes to obtain a hydrolysate comprising a lipid phase and an aqueous phase, b) cooling said hydrolysate to a temperature below 100° C. and separating said lipid phase from said aqueous phase, c) adding a basic compound to said aqueous phase to raise the pH to a value of 2.0 to 8.0, thereby precipitating the acidic ions as salts of low solubility, d) separating said precipitate from said aqueous phase, and e) concentrating the resulting rhamnose containing solution.

2. The method of claim 1, wherein water is the only solvent used in said method.

3. The method of claim 1, wherein said rhamnolipids are obtained by fermentation.

4. The method of claim 1, wherein said method is a continuous process.

5. The method of claim 4, wherein said lipid phase is brought back into said method no later than the hydrolysis step.

6. The method of claim 1, wherein said rhamnolipid emulsion has a conductivity of less than 12 mS/cm.

7. The method of claim 6, wherein said rhamnolipid emulsion has a conductivity of less than 5 mS/cm.

8. The method of claim 1, wherein said emulsion has a total solids content of 5 to 50% by weight.

9. The method of claim 8, wherein said emulsion has a total solids content of 10 to 20% by weight.

10. The method of claim 1, wherein said aqueous acidic rhamnolipid emulsion has a pH of 0.5 to 1.5.

11. The method of claim 1, wherein said hydrolysis is carried out at 110° to 160° C.

12. The method of claim 11, wherein said hydrolysis is carried out at 120° to 150° C.

13. The method of claim 1, wherein said aqueous phase of said resulting hydrolysate is separated from the lipid phase at a temperature of 50° to 90° C.

14. The method of claim 1, wherein the pH of the aqueous phase of step c) is raised to a value of 3.0 to 7.0 by the addition of a basic compound which forms a salt of low solubility with the acid anion contained in the resulting solution.

15. The method of claim 14, wherein said basic compound is $Ca(OH)_2$ and/or $CaCO_3$.

16. The method of claim 1, wherein the aqueous phase which remains after said precipitate is removed in step d) is treated with a decolorizing agent.

17. The method of claim 16, wherein said decolorizing agent is selected from the group consisting of bentonite and activated carbon.

18. The method of claim 1, wherein the rhamnose containing solution is further purified by chromatography on an ion exchange resin.

19. The method of claim 18, wherein the rhamnose containing solution, following ion exchange chromatography, is concentrated to a total solids content of 20 to 60% by weight.

20. The method of claim 19 wherein the rhamnose containing solution is concentrated to a total solids content of 25 to 50% by weight.

21. The process of claim 1, further comprising crystallizing rhamnose monohydrate.

22. The method of claim 21, wherein the crystallization is carried out as a cooling crystallization or an evaporation crystallization.

23. The method of claim 22, wherein the crystallization is a cooling crystallization and the cooling is carried out at a cooling rate of 1° to 10°/hour.

24. The method of claim 23, wherein the cooling is carried out at a cooling rate of 3° to 6°/hour.

25. The method of claim 22, wherein the crystallization is an evaporation crystallization and wherein a supersaturation of 1.05 to 1.3 is maintained in the rhamnose containing solution from which rhamnose monohydrate is crystallized.

26. The method of claim 25, wherein a supersaturation of 1.1 to 1.15 is maintained in the rhamnose containing solution from which rhamnose monohydrate is crystallized.

* * * * *